US012623063B2

(12) United States Patent
Kojima et al.

(10) Patent No.: US 12,623,063 B2
(45) Date of Patent: May 12, 2026

(54) BALLOON FOR BALLOON CATHETER

(71) Applicant: KANEKA CORPORATION, Osaka (JP)

(72) Inventors: Masahiro Kojima, Settsu (JP); Masato Tsueda, Settsu (JP); Yoshinori Nakano, Settsu (JP); Takahisa Hamabuchi, Osaka (JP)

(73) Assignee: KANEKA CORPORATION, Osaka (JP)

( * ) Notice: Subject to any disclaimer, the term of this patent is extended or adjusted under 35 U.S.C. 154(b) by 498 days.

(21) Appl. No.: 18/036,496

(22) PCT Filed: Aug. 16, 2021

(86) PCT No.: PCT/JP2021/029931
§ 371 (c)(1),
(2) Date: May 11, 2023

(87) PCT Pub. No.: WO2022/102189
PCT Pub. Date: May 19, 2022

(65) Prior Publication Data
US 2023/0405289 A1     Dec. 21, 2023

(30) Foreign Application Priority Data

Nov. 16, 2020     (JP) ................................. 2020-190297

(51) Int. Cl.
A61M 25/10         (2013.01)

(52) U.S. Cl.
CPC ...... A61M 25/104 (2013.01); A61M 25/1029 (2013.01); A61M 25/1034 (2013.01);
(Continued)

(58) Field of Classification Search
CPC .......... A61M 25/1029; A61M 25/1034; A61M 25/104; A61M 2025/1031; A61M 2025/1093
See application file for complete search history.

(56) References Cited

U.S. PATENT DOCUMENTS

| | | | |
|---|---|---|---|
| 5,879,369 A | 3/1999 | Ishida | |
| 6,706,010 B1 | 3/2004 | Miki et al. | |

(Continued)

FOREIGN PATENT DOCUMENTS

| | | |
|---|---|---|
| JP | 2004-504111 A | 2/2004 |
| JP | 2005-246097 A | 9/2005 |

(Continued)

OTHER PUBLICATIONS

International Search Report, issued in PCT/JP2021/029931, PCT/ISA/210, dated Sep. 14, 2021.

*Primary Examiner* — John Kim
(74) *Attorney, Agent, or Firm* — Birch, Stewart, Kolasch & Birch, LLP

(57)                    ABSTRACT

Disclosed is a balloon for a balloon catheter that can prevent kinking or buckling of the balloon and elongation of the balloon in the longitudinal direction. A balloon (2) for a balloon catheter has a balloon body (20); the balloon body (20) has an inflating part (20*e*), a distal sleeve part (25), and a proximal sleeve part (21); the distal sleeve part (25) has a fixed part (25*f*) fixed to the shaft (3); the balloon (2) has a reinforcing part (60) disposed on an inner surface of the distal sleeve part (25) at a part of a circumferential direction of the distal sleeve part (25); the reinforcing part (60) is located proximal to a distal end of the fixed part (25*f*); and the balloon (2) does not have the reinforcing part (60) on an inner surface of the proximal sleeve part (21).

9 Claims, 3 Drawing Sheets

(52) U.S. Cl.
CPC ............... *A61M 2025/1031* (2013.01); *A61M 2025/1093* (2013.01)

(56)                    References Cited

U.S. PATENT DOCUMENTS

| | | | |
|---|---|---|---|
| 2002/0010489 A1 | 1/2002 | Grayzel et al. |
| 2005/0102020 A1 | 5/2005 | Grayzel et al. |
| 2006/0015133 A1 | 1/2006 | Grayzel et al. |
| 2007/0106216 A1 | 5/2007 | Noddin |
| 2010/0286721 A1 | 11/2010 | Goodin et al. |
| 2011/0077677 A1 | 3/2011 | Grayzel et al. |
| 2011/0213401 A1 | 9/2011 | Grayzel et al. |
| 2015/0057740 A1 | 2/2015 | Noddin |
| 2015/0141917 A1 | 5/2015 | Tilson et al. |
| 2017/0266420 A1 | 9/2017 | Tsukamoto et al. |
| 2018/0085562 A1 | 3/2018 | Grayzel et al. |
| 2019/0134360 A1 | 5/2019 | Sato et al. |
| 2019/0192832 A1 | 6/2019 | Tilson et al. |

FOREIGN PATENT DOCUMENTS

| | | | |
|---|---|---|---|
| JP | 2008-264569 A | 11/2008 |
| JP | 2009-513299 A | 4/2009 |
| JP | 2015-518776 A | 7/2015 |
| WO | WO 2017/158735 A1 | 9/2017 |
| WO | WO 2018/008514 A1 | 1/2018 |

[FIG. 1]
[FIG. 2]
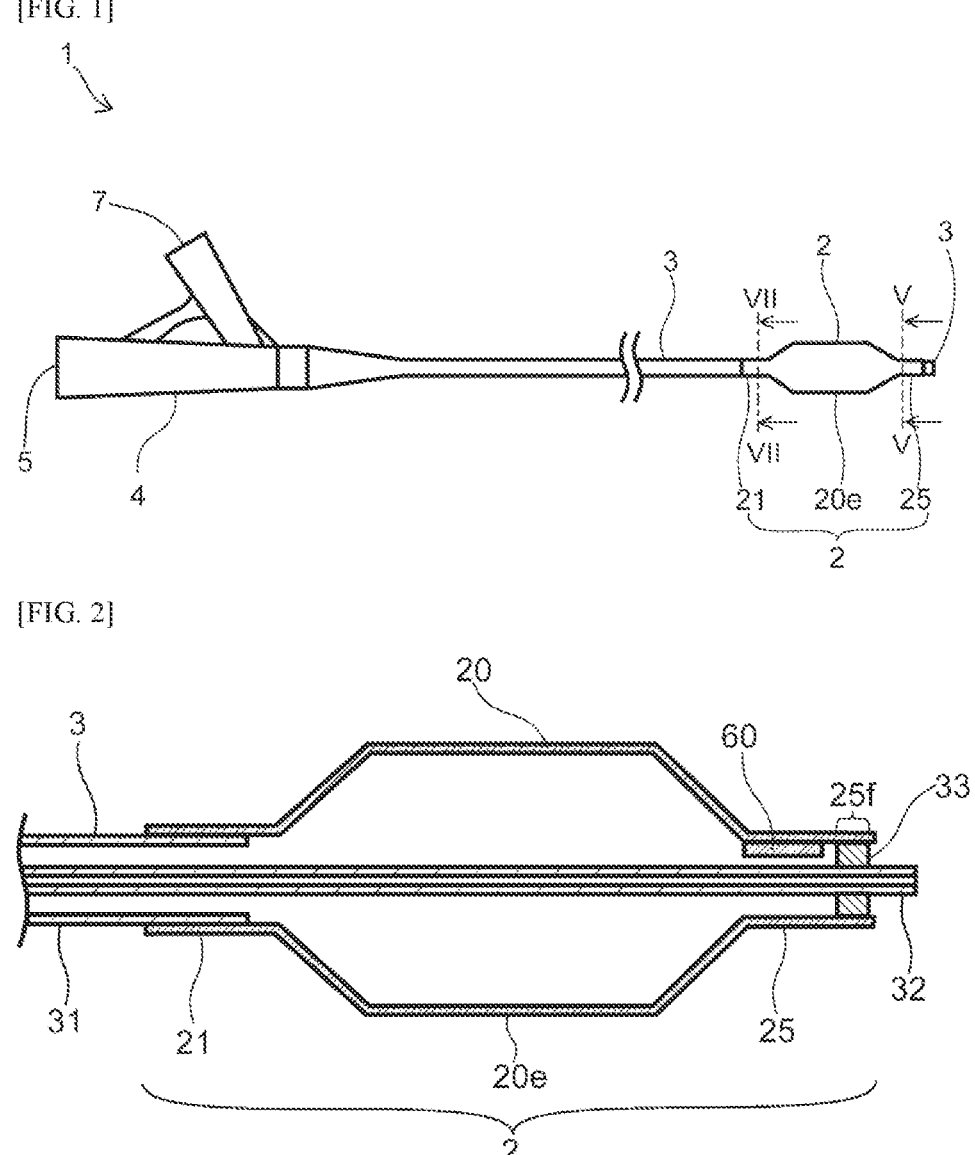

[FIG. 3]
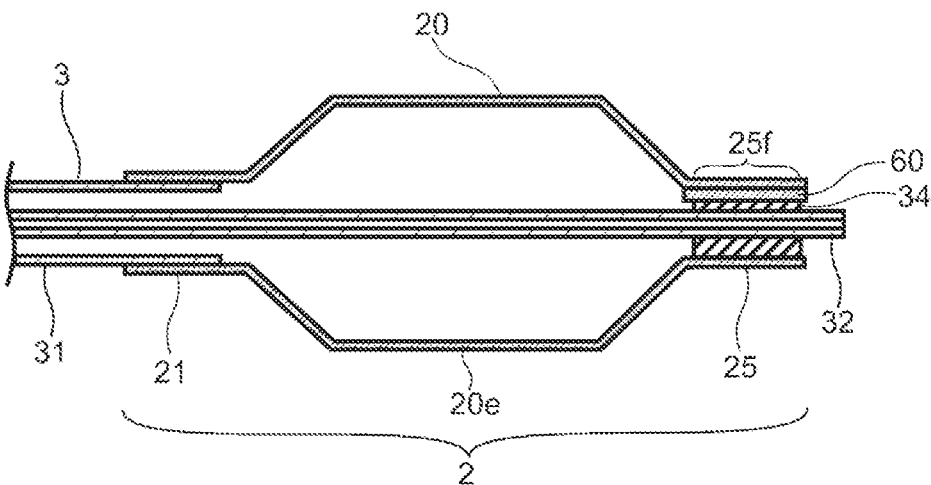
[FIG. 4]
[FIG. 5]
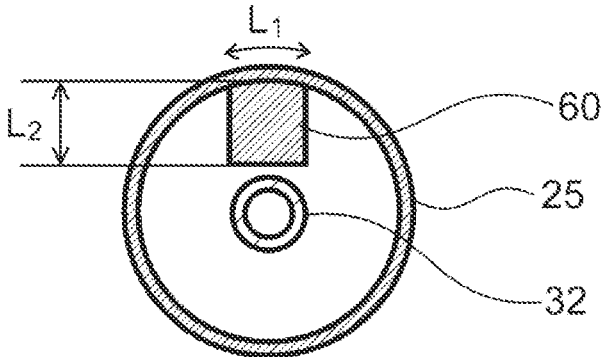

[FIG. 6]
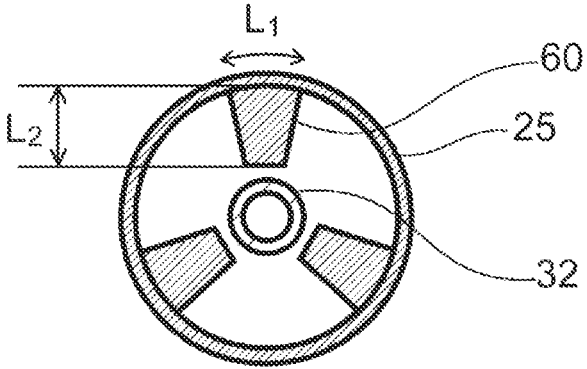
[FIG. 7]
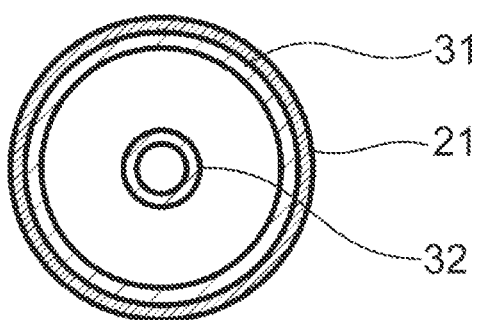
[FIG. 8]
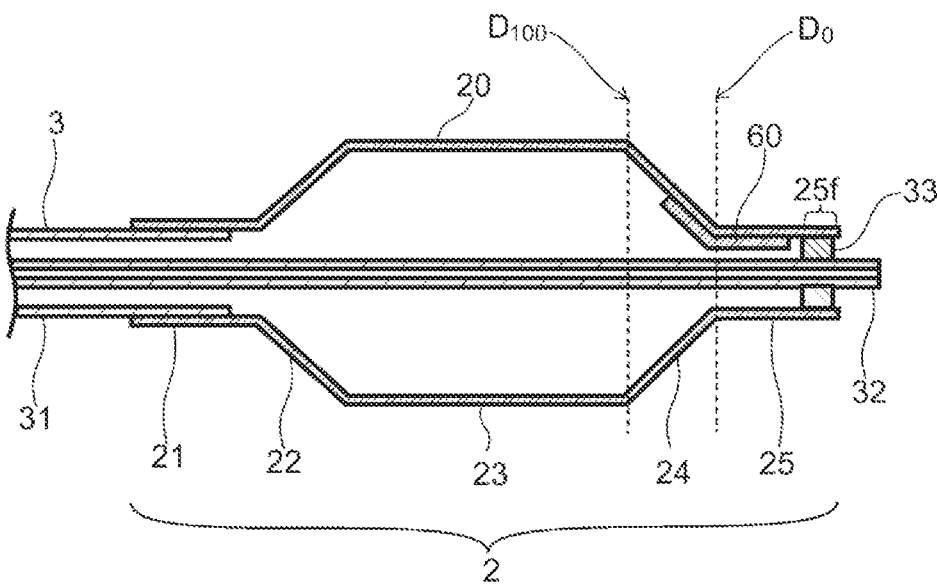

BALLOON FOR BALLOON CATHETER

TECHNICAL FIELD

The present invention relates to a balloon catheter for a balloon catheter.

BACKGROUND ART

One treatment for diseases such as angina pectoris and myocardial infarction caused by narrowing of blood vessels is angioplasty, in which a balloon catheter is used to dilate the narrowed area. In addition, various types of balloon catheters have been proposed for the purpose of dilating the narrowed part of body cavities other than blood vessels such as trachea and gastrointestinal tract. Treatment using balloon catheters is widely used because it is a minimally invasive therapy that does not require open chest surgery like bypass surgery.

Balloon catheters are often inserted away from the lesion to be treated. For example, when delivering a balloon catheter to the heart, the balloon catheter is mainly inserted through the femoral artery or arteries of the wrist or upper arm. Therefore, for safe treatment, the balloon catheter is required to easily travel in the desired direction while following the curved narrow body cavity from the insertion point to the lesion. For example, Patent document 1 discloses a balloon catheter having improved trackability (the ability of the balloon to follow the meandering blood vessel) by employing a multilayer structure of a base material and a coating layer more flexible than the base layer to provides strength and flexibility. Patent document 2 discloses a balloon catheter with a tip having a tapered shape and a distal tapered part having a continuously thinned wall thickness for the purpose of making the tip more flexible and smaller in diameter. Patent document 3 discloses a balloon catheter with a tip made of flexible resin.

RELATED ART DOCUMENT

Patent Document

Patent Document 1: JP 2005-246097 A
Patent Document 2: JP 2008-264569 A
Patent Document 3: WO 2017/158735

SUMMARY OF THE INVENTION

Problems to be Solved by the Invention

In order to safely perform a desired treatment using a balloon catheter, the balloon catheter is required to be easily delivered to the desired treatment site while following the body cavity according to the surgeon's manipulation. However, although the above balloons have certain strength and flexibility to improve trackability to some extent, there was room for improvement in terms of preventing a balloon from kinking, buckling, and elongating in the longitudinal axis direction of the balloon. Accordingly, the objective of the present invention is to provide a balloon for a balloon catheter that can prevent kinking and buckling of the balloon and elongation of the balloon in the longitudinal axis direction and can be easily operated.

Means for Solving the Problems

One embodiment of a balloon for a balloon catheter of the present invention that can solve the above problems has a balloon body having an inflating part, a distal sleeve part located distal to the inflating part, and a proximal sleeve part located proximal to the inflating part, the distal sleeve part having a fixed part that is to be fixed to a shaft; and has a reinforcing part disposed on an inner surface of the distal sleeve part at a part of a circumferential direction of the distal sleeve part, wherein the reinforcing part is disposed proximal to a distal end of the fixed part; and the balloon does not have the reinforcing part on an inner surface of the proximal sleeve part.

Preferably, in the above-described balloon for a balloon catheter, the inflating part has a straight tubular part and a distal tapered part located distal to the straight tubular part; a distal end of the distal tapered part is termed as a position of 0%, and a proximal end of the distal tapered part is termed as a position of 100% in a longitudinal axis direction of the inflating part; and the balloon has the reinforcing part disposed on an inner surface of the distal tapered part at a part of a circumferential direction of the distal tapered part in a section from the position of 0% to a position of 10% of the distal tapered part.

Preferably, in the above-described balloon for a balloon catheter, the reinforcing part in the distal sleeve part and the reinforcing part in the distal tapered part extend continuously in a longitudinal axis direction of the balloon body.

Preferably, in the above-described balloon for a balloon catheter, the reinforcing part is made of resin.

Preferably, in the above-described balloon for a balloon catheter, the reinforcing part is made of metal.

Effects of the Invention

The above-described balloon for a balloon catheter can prevent kinking of the balloon or buckling in the longitudinal axis direction during catheter operation such as delivery of the balloon catheter or treatment operation, and can also prevent elongation of the balloon in the longitudinal axis direction such as when introducing fluid such as pressurized fluid into the balloon to inflate the balloon. In addition, when inflating or deflating the balloon by introducing or discharging the fluid into or out of the balloon, the introduction and discharge time of the fluid (inflation and deflation times) can be prevented from prolonging to avoid treatment delays.

BRIEF DESCRIPTION OF THE DRAWINGS

FIG. 1 is a side view of a balloon catheter in accordance with one embodiment of the present invention.

FIG. 2 is a cross-sectional view of a distal part of the balloon catheter shown in FIG. 1 in the longitudinal axis direction.

FIG. 3 is a cross-sectional view of a distal part of a balloon catheter in accordance with another embodiment of the present invention in the longitudinal axis direction.

FIG. 4 is a cross-sectional view of a distal part of a balloon catheter in accordance with still another embodiment of the present invention in the longitudinal axis direction.

FIG. 5 is a V-V cross-sectional view of FIG. 1.

FIG. 6 is a cross-section view of a variation of FIG. 5.

FIG. 7 is a VII-VII cross-sectional view of FIG. 1.

FIG. 8 is a cross-sectional view of a balloon catheter in accordance with still another embodiment of the present invention in the longitudinal axis direction.

MODE FOR CARRYING OUT THE INVENTION

Hereinafter, the present invention will be described based on the following embodiments, however, the present invention is not limited by the following embodiments and can be altered in design within a scope in compliance with the intent described above and below, and all the changes are to be encompassed within a technical scope of the present invention. Note that, in each drawing, hatching, reference signs for components, and the like may be omitted for convenience of description, and in such a case, the specification and other drawings are to be referred to. Furthermore, since the dimensions of the various components in the drawings are provided for the purpose of facilitating the understanding of the feature of the present invention, the dimensions may differ from the actual dimensions in some cases.

A balloon for a balloon catheter in accordance with one embodiment of the present invention has a balloon body having a inflating part, a distal sleeve part located distal to the inflating part, and a proximal sleeve part located proximal to the inflating part, the distal sleeve part having a fixed part that is to be fixed to a shaft; and has a reinforcing part disposed on the inner surface of the distal sleeve part at a part of a circumferential direction of the distal sleeve part, wherein the reinforcing part is disposed proximal to a distal end of the fixed part; and the balloon does not have the reinforcing part on the inner surface of the proximal sleeve part. Thus, the balloon has the reinforcing part disposed proximal to the distal end of the fixed part on the inner surface of the distal sleeve part at a part of the circumferential direction can improve stiffness while reducing the outer diameter of the distal sleeve part. This can mitigate the difference in stiffness between the distal sleeve part and the fixed part, thereby preventing kinking and buckling of the balloon in the longitudinal axis direction during balloon catheter operation such as delivery of the balloon catheter to the lesion site or treatment operation. In addition, the inner surface of the distal sleeve part has the reinforcing part, which ensures the stiffness of the distal sleeve part that is the destination of the fluid and receives the fluid when a fluid such as pressurized fluid is introduced into the balloon to inflate the balloon, thereby preventing or reducing elongation of the balloon in the longitudinal axis direction. Furthermore, the inner surface of the proximal sleeve part does not have the reinforcing part, which ensures that the lumen of the proximal sleeve part, which serves as the entrance and exit of the fluid to the balloon, is not narrowed, thereby avoiding treatment delays by preventing the introduction and discharge times of the fluid (inflation and deflation times) from prolonging when the balloon is inflated or deflated by introducing or discharging the fluid. Hereinafter, the balloon for a balloon catheter may be referred to as merely "balloon".

Referring to FIGS. 1 to 7, the balloon for a balloon catheter is explained. FIG. 1 is a side view of a balloon catheter in accordance with one embodiment of the present invention. FIG. 2 is a cross-sectional view of a distal part of the balloon catheter shown in FIG. 1 in the longitudinal axis direction. FIG. 3 is a cross-sectional view of a distal part of a balloon catheter in accordance with another embodiment of the present invention, and FIG. 4 is a cross-sectional view of a distal part of a balloon catheter in accordance with still another embodiment of the present invention. FIG. 5 is a V-V cross-sectional view of FIG. 1, and FIG. 6 is a cross-sectional view of a variation of FIG. 5. FIG. 7 is a VII-VII cross-sectional view of FIG. 1.

As shown in FIG. 1, a balloon catheter 1 has a shaft 3 and a balloon 2 disposed outside the shaft 3. The balloon catheter 1 has a proximal side and a distal side, and the balloon 2 is disposed at the distal side of the shaft 3. Note that the proximal side refers to the direction towards a user's or operator's hand in the extending direction of the balloon catheter 1 or the longitudinal axis direction of the shaft 3, and the distal side refers to the opposite side of the proximal side, that is, the direction toward the person to be treated.

As shown in FIGS. 1 to 7, the balloon 2 for a balloon catheter has a balloon body 20, and the balloon body 20 has a inflating part 20e, a distal sleeve part 25 located distal to the inflating part 20e, and a proximal sleeve part 21 located proximal to the inflating part 20e; the distal sleeve part 25 has a fixed part 25f that is to be fixed to the shaft 3, and the balloon 2 has a reinforcing part 60 that is disposed on an inner surface of the distal sleeve part 25 at a part of the circumferential direction of the distal sleeve part 25 and that is disposed proximal to the distal end of the fixed part 25f, and does not have the reinforcing part 60 on an inner surface of the proximal sleeve part 21.

Of the balloon body 20, the inflating part 20e is the portion that is inflatable by introducing fluid. The proximal sleeve part 21 and distal sleeve part 25 are portions that are non-inflatable located proximal and distal to the inflating part 20e, respectively, and the distal sleeve part 25 has the fixed part 25f that is to be fixed to the shaft 3. The shaft 3 preferably has a flow path for the fluid inside, and further has a guidewire insertion path. Configurations in which the shaft 3 has an internal fluid flow path and a guidewire insertion path include, for example, as shown in FIGS. 2 to 4, a configuration in which the shaft 3 has an outer tube 31 and an inner tube 32, and the inner tube 32 serves as the guidewire insertion path and the space between the inner tube 32 and the outer tube 31 serves as the fluid flow path. In the case where the shaft 3 has the outer tube 31 and the inner tube 32, preferably, the inner tube 32 extends through the distal end of the outer tube 31 and penetrates the balloon 2 to the distal side, the inner surface of the distal sleeve part 25 is fixed to the inner tube 32 at the fixed part 25f, and the inner surface of the proximal sleeve part 21 is fixed to the outer tube 31. In this case, at least a part of the proximal sleeve part 21 and at least a part of the distal sleeve part 25 are preferably fixed to the shaft 3 by welding. The distal sleeve part 25 and the inner tube 32 of the shaft 3 may be directly fixed or indirectly fixed via the reinforcing part 60. In addition, the distal sleeve part 25 and the inner tube 32 may be fixed via a fixing member 33 such as another tube as shown in FIG. 2, or may be fixed by welding using another resin 34 as shown in FIG. 3 and the reinforcing part 25f may include both portions fixed via resin 34 and fixed via the resin 34 and the reinforcing part 60. Furthermore, as shown in FIG. 4, the distal sleeve part 25 and the inner tube 32 may be fixed so that the entire longitudinal axial extent of the fixed part 25f includes the resin 34 and the reinforcing part 60. With the above configuration, the inflation and deflation of the inflating part 20e can be controlled using an indeflator (pressurizer for balloons). The fluid may be a pressurized fluid pressurized by a pump or the like.

The distal sleeve part 25 having the reinforcing part 60 disposed on the inner surface of the distal sleeve part 25 and proximal to the distal end of the fixed part 25f at a part of the circumferential direction can improve the stiffness of the distal sleeve part 25 by the reinforcing part 60 while reducing the outer diameter of the distal sleeve part 25. This can mitigate the difference in stiffness between the fixed part 25f and the part of the distal sleeve 25 proximal to the fixed part, which prevents the distal part of the balloon 2 from kinking and buckling. If the distal part of the balloon 2 is less likely to kink or buckle, it is easier to deliver the balloon catheter 1 to the desired site and perform the desired treatment operation. In addition, the reinforcing part 60 disposed on the inner surface of the distal sleeve part 25 can improve the stiffness of the distal sleeve part 25, which is the destination that receives the pressurized fluid introduced from the proximal side of the balloon 2, thereby preventing or reducing elongation of the balloon 2 in the longitudinal axis direction when the pressurized fluid is introduced into the balloon 2 to inflate the balloon 2. This allows the balloon 2 to be fully inflated in the radial direction, and can reduce the risk of balloon 2 inflating into and damaging normal blood vessels that is not to be treated. Furthermore, the reinforcing part 60 is not disposed in the inner surface of the proximal sleeve part 21, which ensures that the lumen of the proximal sleeve part 21, which serves as the entrance and exit of the fluid to the balloon 2 when the pressurized fluid is introduced into the balloon 2 and the fluid is discharged from the balloon 2, is not narrowed, thereby avoiding treatment delays by preventing the introduction and discharge times of the fluid (inflation and deflation times) from prolonging and reducing the burden on the patient.

As shown in FIG. 2, the distal sleeve part 25 may have the reinforcing part 60 spaced apart from the fixed part 25f. In other words, the distal end of the reinforcing part 60 is located more proximally separated from the proximal end of the fixed part 25f. When the reinforcing part 60 is spaced apart from the fixed part 25f, the stiffness of the distal sleeve part 25 can be increased without compromising the flexibility of the balloon 2, making the balloon 2 more flexible and less prone to kinking or buckling. Alternatively, the reinforcing part 60 may be provided contiguous with the fixed part 25f. When the reinforcing part 60 is provided contiguous with the fixed part 25f, the stiffness of the distal sleeve part 25 can be further improved, making the balloon 2 more resistant to kinking and buckling. As shown in FIGS. 3 and 4, the distal sleeve part 25 may also have the reinforcing part in the fixed part 25f, and as shown in FIG. 4, the reinforcing part 60 may be provided continuously from the proximal side to distal side of the fixed part 25f Furthermore, as shown in FIG. 4, the distal sleeve part 25 may have the reinforcing part 60 distal to the distal end of the fixed part 25f, as long as it has the reinforcing part 60 proximal to the distal end of the fixed part. This can further increase the stiffness of the distal sleeve part 25.

The balloon 2 for a balloon catheter preferably has the reinforcing part 60 in 10% or longer of the length of the distal sleeve part 25 in the longitudinal axis direction, more preferably 15% or longer, and even more preferably 20% or longer. The balloon 2 for a balloon catheter may have the reinforcing part 60 in 100% of the length of the distal sleeve part 25 in the longitudinal axis direction, but preferably 95% or shorter, more preferably 90% or shorter, and even more preferably 85% or shorter. When the balloon 2 for a balloon catheter has the reinforcing part 60 on the inner surface of the distal sleeve part 25 in the above range, the stiffness of the distal sleeve part 25 can be improved.

In the case where the reinforcing part 60 is provided at a part of the distal sleeve part in the longitudinal axis direction, the reinforcing part 60 is preferably provided on the side of the proximal end of the distal sleeve part 25. For example, the reinforcing part 60 is preferably provided in 90% or more of the portion proximal to the midpoint of the distal sleeve part 25 in the longitudinal axis direction, more preferably 95% or more, and may be provided in 100%. In this case, the reinforcing part 60 may not be provided in the portion distal to the midpoint of the distal sleeve part 25, or may be provided in 5% or more of the portion distal to the midpoint of the distal sleeve part 25, or may be 10% or more, or may be 15% or more, and may be provided in 50% or less of the portion distal to the midpoint of the distal sleeve part 25, or may be 40% or less, or may be 30% or less. This can improve the stiffness of the inlet side of the pressurized fluid of the distal sleeve part 25, which receives the pressurized fluid introduced from the proximal side of the balloon 2 when the pressurized fluid is introduced into the balloon 2 to inflate the balloon 2, thereby making it easier to reduce elongation of the balloon 2 in the longitudinal axis direction.

In the case where the reinforcing part 60 is provided in a part of the distal sleeve part in the longitudinal axis direction, the distal end of the reinforcing part 60 is preferably located proximal to the distal end of the fixed part 25f, and the proximal end of the reinforcing part 60 is preferably located proximal to the proximal end of the fixed part 25f. This allows the inner surface of the distal sleeve part 25 to be configured in the following order from the proximal side in the longitudinal axis direction: portion with the reinforcing part 60, portion with the reinforcing part 60 and the fixed part 25f, and portion with the fixed part 25f, thereby making the change in stiffness of the distal sleeve part 25 gradual. As a result, the stiffness step of the distal sleeve part 25 can be mitigated, making kinking and buckling of the distal part of the balloon 2 more difficult to occur.

Alternatively, in the case where the reinforcing part 60 is provided in a part of the distal sleeve part 25 in the longitudinal axis direction, the distal end of the reinforcing part 60 may be located proximal to the proximal end of the fixed part 25f, and in this case, the distal end of the reinforcing part 60 may be spaced apart from the proximal end of the fixed part 25f as described above, or alternatively, the distal end of the reinforcing part 60 may be configured to contact the proximal end of the fixed part 25f. When the distal end of the reinforcing part 60 is provided to be adjoining the proximal end of the fixed part 25f, the distal sleeve part 25 can have the portion that is stiffened by the reinforcing part 60 and the portion that is stiffened by the fixed part 25f continuously, making the change in stiffness of the distal sleeve part 25 gradual. As a result, the stiffness step of the distal sleeve part 25 can be mitigated, making kinking and buckling of the distal part of the balloon 2 more difficult to occur.

The cross-sectional shape of the reinforcing part 60 perpendicular to the longitudinal axis direction may be any shape, and may be approximate triangle or approximate rectangle as shown in FIG. 5, approximate trapezoid as shown in FIG. 6, polygon, fan shape, wedge shape, convex shape, spindle shape, or the like. In the radial cross-section perpendicular to the longitudinal axis direction of the balloon body 20, when the maximum length of the reinforcing part 60 on a straight line connecting the center of the balloon body 20 and the circumference of the balloon body 20 is defined as a height $L_2$ of the reinforcing part 60, the height $L_2$ of the reinforcing part 60 is preferably 1 time or more the film thickness of the balloon body 20, more preferably 1.5 times or more, even more preferably 2 times or more, and is acceptable to be 50 times or less, 30 times or less, or 10 times or less. The reinforcing part 60 with such a height $L_2$ can improve the stiffness of the distal sleeve part 25. In addition, in the radial cross-section of the reinforcing part 60 perpendicular to the longitudinal axis direction, the reinforcing part 60 has a length $L_1$ in the circumferential direction of the balloon 2, and preferably satisfies the relationship $L_2 > L_1$. This can further improve the stiffness of the distal sleeve part 25. $L_1$ and $L_2$ may satisfy $L_2 > 0.8L_1$, $L_2 > 0.5L_1$, or $L_2 > 0.3L_1$. When $L_1$ and $L_2$ satisfy the above relationship, the stiffness of the distal sleeve part can be improved.

Alternatively, the reinforcing part 60 may be configured so that $L_1$ and $L_2$ satisfy $L_2 < L_1$. With such a configuration, it is possible to balance the stiffness between the portion of the distal sleeve part 25 with and without the reinforcing part 60, making it possible to achieve an appropriate stiffness as a whole.

As shown in FIG. 5, the balloon 2 for a balloon catheter may have one reinforcing part 60 on the inner surface of the distal sleeve part 25 in the circumferential direction. Alternatively, as shown in FIG. 6, the balloon 2 for a balloon catheter may have a plurality of the reinforcing parts 60 on the inner surface of the distal sleeve part 25 in the circumferential direction. When having a plurality of the reinforcing parts 60, each reinforcing part 60 is preferably spaced apart from each other in the circumferential direction, and more preferably they are equally spaced in the circumferential direction. The balloon 2 for a balloon catheter having a plurality of the reinforcing parts 60 in such a way can improve the stiffness of the distal sleeve part 25 evenly in the circumferential direction, and thus, preventing kinking and buckling of the distal part of the balloon 2 and elongation of the balloon 2 in any direction in the circumferential direction.

Although not shown in the figures, the balloon 2 for a balloon catheter may have the reinforcing part 60 that extends discontinuously in the longitudinal axis direction of the balloon body 20 on the inner surface of the distal sleeve part 25 at a part of the circumferential direction of the distal sleeve part 25, or may have the reinforcing part 60 that extends spirally with respect to the longitudinal axis of the balloon body 20. By adjusting the arrangement of the reinforcing part 60, the stiffness of the distal sleeve part 25 can be adjusted.

The reinforcing part 60 is preferably made of resin. The reinforcing part 60 made of resin can ensure the stiffness of the distal sleeve part 25 without excessively compromising its flexibility. The resin forming the reinforcing part 60 includes, for example, polyolefin-based resin such as polyvinyl chloride, polyethylene, polypropylene, and cyclic polyolefin; polystyrene-based resin; polymethylpentene-based resin such as poly-(4-methylpentene-1); polycarbonate-based resin; acrylic resin; ABS-based resin; polyester resin such as polyethylene terephthalate and polyethylene naphthalate; butadiene-styrene copolymer, polyamide-based resin such as polyamide elastomer, nylon 6, nylon 6●6, nylon 6●10, and nylon 12. Only one of these may be used, or two or more may be used in combination. In the case where the reinforcing part 60 is made of resin, the reinforcing part 60 is preferably fixed to the balloon body 20 by, for example, adhesive bonding or welding, and more preferably fixed by welding. Alternatively, the reinforcing part 60 may be integrally molded with the balloon body 20. When integrally molded, the reinforcing part 60 can be prevented from falling from the balloon body 20.

The reinforcing part 60 is preferably made of metal. When the reinforcing part 60 is made of metal, the stiffness of the distal sleeve part 25 can be easily adjusted by the shape, number, and arrangement of the reinforcing part 60. The metal forming the reinforcing part includes, for example, stainless steel, aluminum, aluminum alloy, titanium, titanium alloy, copper, copper alloy, tantalum, and cobalt alloy. Only one of these may be used, or two or more may be used in combination. When the reinforcing part 60 is made of metal, the reinforcing part 60 can be fixed to the balloon body 20 by, for example adhesive bonding.

Preferably, the balloon 2 for a balloon catheter does not have the reinforcing part 60 on the outer surface of the distal sleeve part 25. This allows the outer diameter of the distal sleeve part 25 to be small, allowing the balloon catheter 1 to be easily inserted into the body cavity. Alternatively, although not shown in the figures, the balloon 2 for a balloon catheter may have a portion having the reinforcing part 60 on the outer surface of the distal sleeve 25. In this case, when the maximum length of the reinforcing part 60 on a straight line connecting the center of the balloon body 20 and the circumference of the balloon body 20 in a radial cross-section perpendicular to the longitudinal axis direction of the balloon body 20 is defined as the height of the reinforcing part 60, the height of the reinforcing part 60 is preferably lower than the height $L_2$ of the reinforcing part 60 on the inner surface of the distal sleeve part With such a configuration, the outer diameter of the distal sleeve part 25 does not become too large even if the distal sleeve part 25 has the reinforcing part 60 on the outer surface, and the stiffness of the distal sleeve part 25 can be improved by the reinforcing part on the inner and outer surfaces, further preventing kinking and buckling of the distal part of the balloon 2 and elongation of the balloon 2 while ensuring the insertion of the balloon catheter 1.

As shown in FIG. 7, the balloon 2 for a balloon catheter does not have the reinforcing part 60 on the inner surface of the proximal sleeve part 21. This allows the lumen of the proximal sleeve part 21 to be sufficiently secured so that the fluid can easily pass through the lumen of the proximal sleeve part 21, which serves as the entrance and exit to the balloon 2, when introducing pressurized fluid into or discharging fluid from the balloon 2, thereby reducing the burden on the patient by shortening the time for introducing and discharging the fluid.

Although not shown in the figures, the balloon 2 for a balloon catheter may have the reinforcing part 60 on the outer surface of the proximal sleeve part 21 at a part of the circumferential direction of the proximal sleeve part 21. The reinforcing part 60 disposed on the outer surface of the proximal sleeve part 21 can improve the stiffness of the proximal part of the balloon body 20 without interfering with the introduction or discharge of the fluid.

Referring to FIG. 8, a balloon for a balloon catheter in accordance with still another embodiment of the present invention is explained. FIG. 8 is a cross-sectional view of the balloon catheter in accordance with still another embodiment of the present invention in the longitudinal axis direction.

As shown in FIG. 8, the inflating part 20*e* preferably has a straight tubular part 23 and a distal tapered part 24 located distal to the straight tubular part 23. In addition, the inflating part 20*e* may have a proximal tapered part 22 located proximal to the straight tubular part 23. The distal tapered part 24 and the proximal tapered part 22 are preferably formed so that the diameter decreases as it is away from the straight tubular part 23. Since the inflating part 20*e* has the straight tubular part 23, the straight tubular part 23 can make sufficient contact with the stenosis to facilitate dilation of the stenosis, and since the inflating part 20*e* has the distal tapered part 24 and proximal tapered part 22 whose outer diameters decreases as they are away from the straight tubular part 23, the outer diameters of the distal and proximal part of the balloon 2 can be decreased to reduce the step between the shaft 3 and the balloon 2 when the balloon 2 is deflated and wrapped around the shaft 3, allowing the balloon 2 to be easily inserted into the body cavity.

When the distal end of the distal tapered part 24 is termed as a position of 0% $D_0$ and the proximal end of the distal tapered part 24 is termed as a position of 100% $D_{100}$ in the longitudinal axis direction of the inflating part 20*e*, the balloon 20 preferably has the reinforcing part 60 disposed on an inner surface of the distal tapered part 24 at a part of the circumferential direction of the distal tapered part 24 in the section from the position of 0% to a position of 10% of the distal tapered part 24. The balloon 2 for a balloon catheter that has the reinforcing part 60 also on the inner surface of the distal tapered part 24 in the above range makes it possible to further improve the stiffness without increasing the outer diameter of the distal side of the balloon 2. This prevents kinking or buckling of the balloon 2 also at the distal tapered part 24. In addition, the stiffness of the distal tapered part 24 and the distal sleeve part 25, which are the distal portions that receive the pressurized fluid, can be secured, which further prevents elongation of the balloon 2 in the longitudinal axis direction.

The balloon 2 for a balloon catheter may have the reinforcing part 60 beyond the section from the position of 0% to the position of 10% of the distal tapered part 24, and the section may be to the position of 15% or more, or to the position of 20% or more. The balloon 2 for a balloon catheter may have the reinforcing part 60 in a section from the position of 0% to a position of 95% or less, to a position of 80% or less, or to a position of 70% or less. The balloon 2 for a balloon catheter having the reinforcing part 60 in the above range can improve the stiffness of the distal tapered part 24.

Although not shown in the figures, the balloon 2 for a balloon catheter may have one reinforcing part 60 circumferentially on the inner surface of the distal tapered part 24, or may have a plurality of the reinforcing parts 60. In the case of having a plurality of the reinforcing parts 60, each of the reinforcing parts 60 is preferably spaced apart from each other in the circumferential direction, and more preferably equally spaced in the circumferential direction. The balloon 2 for a balloon catheter having a plurality of the reinforcing parts 60 in such a way can improve the stiffness of the distal tapered part 24 evenly in the circumferential direction, preventing kinking and buckling of the distal part of the balloon 2 and elongation of the balloon 2 in any direction in the circumferential direction.

As shown in FIG. 8, the reinforcing part 60 in the distal sleeve part 25 and the reinforcing part 60 in the distal tapered part 24 preferably extend continuously in the longitudinal axis direction of the balloon body 20. The balloon 2 for a balloon catheter having the reinforcing part 60 that extends continuously from the distal sleeve part 25 to the distal tapered part 24 can further prevent or reduce elongation of the distal part of the balloon 2 in the axis direction.

Materials forming the balloon body 20 include, for example, polyolefin-based resin such as polyethylene, polypropylene, ethylene-propylene copolymer; polyester-based resin such as polyethylene terephthalate and polyester elastomer; polyurethane-based resin such as polyurethane and polyurethane elastomer; polyphenylene sulfide-based resin; polyamide-based resin such as polyamide and polyamide elastomer; fluorine-based resin; silicone-based resin; and natural rubber such as latex rubber. Only one of these may be used, or two or more may be used in combination. Of these, polyamide-based resin, polyester-based resin, and polyurethane-based resin are preferably used. In particular, elastomer resin is preferably used from the viewpoint of thinning and flexibility of the balloon body 20. For example, among polyamide-based resins, nylon 12, nylon 11, and the like are suitable for the resin forming the balloon body 20, and more preferably nylon 12 because it is relatively easy to mold when blow molding. Polyamide elastomers such as polyether ester amide elastomer and polyamide ether elastomer are also preferred in terms of thinning and flexibility of the balloon body 20. Of these, polyether ester amide elastomer is preferred in terms of high yield strength and good dimensional stability of the balloon body 20.

Materials forming the shaft 3 include, for example, polyamide-based resin, polyester-based resin, polyurethane-based resin, polyolefin-based resin, fluorine-based resin, polyvinyl chloride-based resin, silicone-based resin, and natural rubber. Only one of these may be used, or two or more may be used in combination. Of these, the material forming the shaft 3 is preferably at least one of polyamide-based resin, polyolefin-based resin, and fluorine-based resin. This can improve surface slipperiness of the shaft 3 and improve the insertion of the balloon catheter 1 into the body cavity.

The balloon 2 and the shaft 3 may be joined by adhesive bonding, welding, or by attaching a ring-shaped member at the point where the end of the balloon 2 and the shaft 3 overlap to swage them. Of these, the balloon 2 and the shaft 3 are preferably joined by welding. By welding the balloon 2 and the shaft 3, the bond between the balloon 2 and the shaft 3 is difficult to be released even when the balloon 2 is repeatedly inflated and deflated, easily increasing the strength of the bond between the balloon 2 and the shaft 3.

As shown in FIG. 1, a hub 4 may be provided at a proximal side of the shaft 3, and the hub 4 may be provided with a fluid inlet 7 that is connected to the flow channel of the fluid supplied to the interior of the balloon 2. In addition, the hub 4 preferably has a guidewire insertion port 5 that is connected to the guidewire insertion channel. The balloon catheter 1 having the hub 4 provided with the fluid inlet 7 and the guidewire insertion port 5 can facilitate the operation of supplying fluid inside the balloon 2 to inflate and deflate the balloon 2 and delivering the balloon catheter 1 to a lesion site along a guidewire. The balloon 2 in accordance with embodiments of the present invention is applicable not only to the above-described balloon catheter, which is a so-called over-the-wire balloon catheter in which the guidewire is inserted over the distal to the proximal side of the shaft, but also to a so-called rapid exchange balloon in which the guidewire is inserted from the distal side to the midway of the proximal side of the shaft 3.

The joining of the shaft 3 and the hub 4 may be, for example, adhesive bonding or welding. Of these, the shaft 3 and the hub 4 are preferably joined by adhesive bonding. The adhesive bonding of the shaft 3 and the hub 4 can increase the bonding strength of the shaft 3 and the hub 4 to increase durability of the balloon catheter 1 when the materials forming the shaft 3 and the hub 4 are different, for example, in a case where the shaft 3 is made of material having high flexibility and the hub 4 is made of material having high stiffness.

The present application claims priority based on Japanese Patent Application No. 2020-190297 filed on Nov. 16, 2020. All the contents described in Japanese Patent Application No. 2020-190297 filed on Nov. 16, 2020 are incorporated herein by reference.

DESCRIPTION OF REFERENCE SIGNS

1: balloon catheter
2: balloon
3: shaft
4: hub
5: guidewire insertion port
7: fluid inlet 20: balloon body
20e: inflating part
21: proximal sleeve part
22: proximal tapered part
23: straight tubular part
24: distal tapered part
25: distal sleeve part
25f: fixed part
31: outer tube
32: inner tube
33: fixing member
34: resin at the fixed part
60: reinforcing part
$D_0$: position of 0%
$D_{100}$: position of 100%
$L_1$: length of the reinforcing part in the circumferential direction of the balloon
$L_2$: height of the reinforcing part

The invention claimed is:

1. A balloon for a balloon catheter, comprising:
a balloon body having an inflating part, a distal sleeve part located distal to the inflating part, and a proximal sleeve part located proximal to the inflating part, the distal sleeve part having a fixed part configured to be fixed to a shaft; and
a reinforcing part disposed on an inner surface of the distal sleeve part so that the reinforcing part extends in a longitudinal axis direction of the distal sleeve part and partially covers the inner surface of the distal sleeve part in a circumferential direction of the distal sleeve part, wherein
the reinforcing part is disposed proximal to a distal end of the fixed part.

2. The balloon for a balloon catheter according to claim 1, wherein
the inflating part has a straight tubular part and a distal tapered part located distal to the straight tubular part, so that the distal tapered part is located between the straight tubular part and the distal sleeve part in a longitudinal axis direction of the inflating part, and
the reinforcing part is further disposed on an inner surface of the distal tapered part so that the reinforcing part partially covers the inner surface of the distal tapered part in a circumferential direction of the distal tapered part and extends along the inner surface of the distal tapered part in a section from a position of 0% to a position of 10% of the distal tapered part in a longitudinal axis direction of the distal tapered part, where a distal end of the distal tapered part is defined as the position of 0%, and a proximal end of the distal tapered part is defined as a position of 100% in the longitudinal axis direction of the distal tapered part.

3. The balloon for a balloon catheter according to claim 2, wherein the reinforcing part continuously extends from the distal sleeve part to the distal tapered part in a longitudinal axis direction of the balloon body.

4. The balloon for a balloon catheter according to claim 2, wherein the reinforcing part is made of resin.

5. The balloon for a balloon catheter according to claim 2, wherein the reinforcing part is made of metal.

6. The balloon for a balloon catheter according to claim 1, wherein the reinforcing part is made of resin.

7. The balloon for a balloon catheter according to claim 1, wherein the reinforcing part is made of metal.

8. The balloon for a balloon catheter according to claim 1, wherein
the inflating part has a straight tubular part and a distal tapered part located distal to the straight tubular part, so that the distal tapered part is located between the straight tubular part and the distal sleeve part in a longitudinal axis direction of the inflating part;
the reinforcing part is not disposed on an inner surface of the distal tapered part in a section from a position of 70% to a position of 100% of the distal tapered part in a longitudinal axis direction of the distal tapered part, where a distal end of the distal tapered part is defined as a position of 0%, and a proximal end of the distal tapered part is defined as the position of 100% in the longitudinal axis direction of the distal tapered part.

9. The balloon for a balloon catheter according to claim 1, wherein the balloon does not have a reinforcing part on an inner surface of the proximal sleeve part.

* * * * *